ered on SiO₂ was introduced into a tubular reactor (diameter 25 mm, length 500 mm).

United States Patent [19]
Landscheidt et al.

[11] Patent Number: 5,288,894
[45] Date of Patent: Feb. 22, 1994

[54] PROCESS FOR THE PREPARATION OF DIALKYL CARBONATES

[75] Inventors: Heinz Landscheidt, Duisburg; Erich Wolters, Cologne; Alexander Klausener, Stolberg; Heinz-Ulrich Blank, Odenthal; Udo Birkenstock, Ratingen, all of Fed. Rep. of Germany

[73] Assignee: Bayer Aktiengesellschaft, Leverkusen, Fed. Rep. of Germany

[21] Appl. No.: 958,853

[22] Filed: Oct. 8, 1992

[30] Foreign Application Priority Data

Oct. 21, 1991 [DE] Fed. Rep. of Germany ....... 4134688

[51] Int. Cl.⁵ .............................................. C07C 68/06
[52] U.S. Cl. .................................................... 558/277
[58] Field of Search ........................................ 558/277

[56] References Cited

U.S. PATENT DOCUMENTS

| 4,360,477 | 11/1982 | Hallgren et al. | 558/277 |
| 4,663,477 | 5/1987 | Crandall et al. | 560/204 |
| 4,879,401 | 11/1989 | Doumaux, Jr. et al. | 558/488 |

FOREIGN PATENT DOCUMENTS 0425197 5/1991 European Pat. Off. .
3834065 4/1990 Fed. Rep. of Germany .

OTHER PUBLICATIONS

Jiang Xuan-zhen, "Zeitschrift fur katalytische Forschung", vol. 10, Mar. 1989, pp. 75–78.

*Primary Examiner*—Robert W. Ramsuer
*Assistant Examiner*—Jacqueline Haley
*Attorney, Agent, or Firm*—Sprung Horn Kramer & Woods

[57] ABSTRACT

Dialkyl carbonates can be prepared by reaction of carbon monoxide with alkyl nitrites in a continuous gas phase reaction, in which a platinum metal catalyst of oxidic or hydroxidic compounds of elements from group Vb of the Periodic Table (Mendeleev) as supports and, if desired, addition of an antimony, bismuth, aluminium, copper, vanadium, niobium, tantalum, tin, iron, cobalt, nickel compound or a mixture of a plurality thereof on this catalyst are used, and the hydrogen halide which is discharged from the reactor together with the reaction mixture is batchwise or continuously replaced in the course of the reaction. This results in the formation of dialkyl carbonates in almost quantitative selectivity; the corresponding dialkyl oxalates can, in most cases, not be detected.

18 Claims, No Drawings

PROCESS FOR THE PREPARATION OF DIALKYL CARBONATES

BACKGROUND OF THE INVENTION

1. Field Of The Invention

The present invention relates to a process for the preparation of dialkyl carbonates by reaction of carbon monoxide (CO) with alkyl nitrites in the presence of a catalyst from the series of platinum metal halides on a support from the series comprising oxidic or hydroxidic compounds of elements from group Vb of the Periodic Table (vanadium, niobium, tantalum), which catalyst may contain additives comprising compounds of further elements.

Dialkyl carbonates are of general chemical importance. Thus, for example, diethyl carbonate is an excellent solvent in the medium boiling range. Furthermore, dialkyl carbonates are excellent carbonylating and acylating reagents. Finally, they are of great importance in the preparation of other carbonates, of urethanes and of ureas.

2. Description Of The Related Art

The preparation of dialkyl carbonates by reactions of phosgene or alkyl chloroformates with alcohols is known. However, there is an increasing interest in replacing the use of the poisonous phosgene or the intermediates derived thereof, such as the chloroformic ester, by other processes. Apart from experiments to obtain dialkyl carbonates by reaction of CO with lower alcohols, in particular those processes are of importance in which CO are reacted in the gas phase with alkyl nitrite over a platinum metal catalyst. In reactions of this type, apart from the desired dialkyl carbonate, the formation of dialkyl oxalate is always observed.

Thus, EP 425 197 discloses a process which, according to its preferred embodiment, leads to dialkyl carbonates of methanol and ethanol from CO and methyl nitrite and ethyl nitrite in the gas phase over a $PdCl_2$ catalyst on activated carbon. According to this EP 425 197 Table 1, the selectivities to give the desired lower dialkyl carbonates reach values of up to 94%; however, lower dialkyl oxalates and $CO_2$ are always observed as by-products. Moreover, when this process was repeated, the high selectivities mentioned could only be reproduced insufficiently. The catalysts of this EP 425 197 contain additions of chlorides of base metals; a substantial addition of hydrogen chloride, i.e. an amount of 1 to 50 % mol, relative to the platinum metal in the catalyst, is introduced into the system, or a portion of the catalyst has to be removed from the reactor and subjected to a hydrogen chloride treatment.

In order to obtain dimethyl carbonate from CO and methyl nitrite, a carbon support is also used in Zeitschrift für Katalytische Forschung (J. Catalytical Research, Dalian, China), Vol. 10 (1), pp. 75–78 (1989) as support for a $PdCl_2$-containing catalyst, which, however, also always leads to the additional formation of dimethyl oxalate.

A Pd/carbon catalyst is also mentioned in Chin. Sci. Bull. 34 (1989), 875–76 for the preparation of dimethyl carbonate from CO and methyl nitrite.

This preference for a carbon support is not unexpected, since Platinum Metals Review 34 (1990), 178–180 reports, with reference to old literature, that the reaction of a lower alkyl nitrite with CO over a Pd catalyst produces different main products, depending on the support; according to this report, a carbon support predominantly produces dialkyl carbonate, while an oxidic support, such as, for example, an $Al_2O_3$ support mainly produces dialkyl oxalate.

SUMMARY OF THE INVENTION

It has now been found that when CO is reacted with alkyl nitrites, oxidic or hydroxidic compounds of elements from group Vb of the Periodic Table as catalyst support not only unexpectedly leads to the dialkyl carbonates but moreover a significant increase in selectivity to give the desired dialkyl carbonates is obtained to such an extent that, in addition to more than 97% of selectivity, in many case more than 99% of selectivity to give these dialkyl carbonates, it is in general impossible to detect any oxalate whatsoever. Merely a small amount of $CO_2$ can be observed in the reaction mixture. In addition the use of the oxidic and hydroxidic compound of elements from group Vb of the Periodic Table as support, which was not believed to be possible, has the essential advantage of increased stability and abrasion resistance, compared with a supported catalyst based on a carbon support.

A process for the preparation of dialkyl carbonates of the formula $$O=C(OR)_2 \qquad (I),$$

in which
R represents straight-chain or branched $C_1$–$C_4$-alkyl, by reaction of carbon monoxide (CO) with alkyl nitrites of the formula $$RONO \qquad (II),$$

in which
R has the meaning given,
in the presence or absence of an inert gas and in the presence or absence of the parent alcohol ROH and in the presence or absence of No over a platinum metal supported catalyst at elevated temperature in a continuous gas phase reaction has been found, which process is characterised in that the supports used are oxidic or hydroxidic compounds of elements from group Vb of the Periodic Table (Mendeleev), the platinum metal is present in the form of a halide or a halide-containing complex compound, in which the platinum metal halide or the halogen-containing complex comprising the platinum metal can be generated in situ in the process reactor under the reaction conditions from the platinum metal or a halogen-free platinum metal compound by means of hydrogen halide, the catalyst is furthermore provided with or without an addition of an antimony, bismuth, aluminium, copper, vanadium, niobium, tantalum, tin, iron, cobalt, nickel compound or a mixture of a plurality thereof, and the reaction is carried out at a nitrite:CO volume ratio of 0.1–10:1 and a temperature of 50°–150° C., in which the addition of hydrogen halide is continued batchwise or continuously in an amount in which hydrogen halide is discharged from the reactor together with the reaction mixture.

The reaction in the process according to the invention takes place in accordance with the following equation:

$$CO + 2RONO \rightarrow O:C(OR)_2 + 2NO.$$

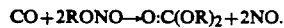

Examples of straight-chain or branched alkyl having 1–4 C atoms are methyl, ethyl, propyl, isopropyl, butyl, isobutyl, preferably the n-alkyls mentioned, particularly preferably methyl and ethyl and very particularly preferably methyl.

In principle, it is possible to start with a mixture of different alkyl nitrites, in which case, however, the product formed is also a mixture of different dialkyl carbonates and possibly asymmetrically substituted dialkyl carbonates. For a uniform reaction, it is therefore preferable to start with only one alkyl nitrite.

While it is in principle possible to react CO with an alkyl nitrite without any further component in the mixture, for example if the composition of the mixture is outside the explosion limits, an inert gas is in many cases used for diluting the reactants. Examples of inert gases are noble gases, nitrogen and carbon dioxide, preferably argon, nitrogen or carbon dioxide, particularly preferably nitrogen and carbon dioxide. The amount of inert gas is 20–80% by volume, preferably 30–70% by volume, relative to the total gas volume to be introduced into the reactor. The inert gas and any unconverted residual amounts of reactants which may be present therein can be recycled.

The volume ratio of the reactants nitrite and CO with respect to one another is 0.1–10:1, preferably 0.2–4:1, particularly preferably 0.3–3:1.

The gas mixture to be reacted can furthermore contain small amounts of alcohol ROH, for example in an amount of 0–10% by volume and small amounts of NO, for example in an amount of 0–10% by volume, both relative to the entire volume of the gas mixture to be used. Such additions of ROH or NO can originate, for example, from the preparation of the alkyl nitrite and be introduced into the reaction gas mixture, for example, together with it.

The catalyst for the process according to the invention is applied to the oxidic or hydroxidic compound from the series comprising elements from group Vb of the Periodic Table (Mendeleev) as a support; in its ready-to-react state, its reactive component comprises the platinum metal halide or the complex compound containing the platinum metal halide. Such complex compounds are generally known and examples thereof are alkali metal chloride complex compounds, such as lithium tetrachloropalladate or sodium tetrachloropalladate, $Li_2[PdCl_4]$ or $Na_2[PdCl_4]$.

Furthermore, it has been found that the platinum metal halide or the complex compound containing the platinum metal halide can be formed in situ in the reactor under the reaction conditions, i.e. An the presence of the gas mixture to be reacted, from metallic platinum metal or a halogen-free platinum metal compound by means of hydrogen halide. Accordingly, the reactor can also be filled with an otherwise comparable catalyst which contains the platinum metal initially in metallic form or was prepared by means of a halogen-free platinum metal compound. Examples of suitable halogen-free platinum metal compounds of this type are platinum metal nitrates, platinum metal propionates, platinum metal butyrates, platinum metal carbonates, platinum metal oxides, platinum metal hydroxides or others known to one skilled in the art.

Elements of the group of platinum metals in the context of the invention are palladium, platinum, iridium, ruthenium and rhodium, preferably palladium, ruthenium and rhodium, particularly preferably palladium.

Halides for the purposes of the invention are fluoride, chloride, bromide and iodide, preferably chloride and bromide, particularly preferably chloride.

The amount of platinum metal halide or complex compound containing the platinum metal halide is 0.01–8% by weight, preferably 0.05–4% by weight, calculated as platinum metal and based on the total weight of the catalyst.

The catalyst for the process according to the invention may be provided with an addition of an antimony, bismuth, aluminium, copper, vanadium, niobium, tantalum, tin, iron, cobalt, nickel compound or a mixture of a plurality thereof; preferably, such an addition is present. Such additions are present in salt-like or in metallic form of the elements mentioned. Similarly, as described above for the platinum metal, for example, the halide form of such additions is formed under the reaction conditions from the metallic form of these additions and hydrogen halide. Preferably, such additives comprise an antimony, bismuth, aluminium, vanadium, niobium, tantalum compound or a mixture of a plurality thereof. Particularly preferably, these additions are present as halides of antimony, bismuth, aluminium, vanadium, niobium, tantalum and particularly preferably as chlorides of antimony, bismuth, aluminium, vanadium, niobium and tantalum. Regarding the hydroxidic or oxidic compounds of the metals from group Vb of the Periodic Table, which, according to the invention act as catalyst support, for example, the following may be mentioned:

Vanadium can occur in the oxidation states +2 to +5, and therefore a wide range of oxidic and hydroxidic compounds as hydroxides, hydrated oxides and oxides also exist. The systems $V_2O_5$, $[VO(H_2O)_5]^{2\oplus}$anion$^{2\ominus}$, $VO_4^{4\ominus}$cation$^{4\oplus}$, $VO_2$, $V_2O_3$ and $VO$ may be mentioned by way of example. The compound $V_2O_5$ may be considered the anhydride of orthovanadic acid $H_3VO_4$, from which the polyvanadic acids are derived by condensation, in accordance with the following equation:

$$nH_3VO_4 \rightleftharpoons (n-1)H_2O + H_{n+2}V_nO_{3n+1},$$

in which n is any desired natural number. Depending on the pH range, various species derived therefrom exist, such as, for example:

$$HVO_4^{2\ominus}, HV_2O_7^{3\ominus}, V_3O_8^{6\ominus}, HV_{10}O_{28}^{5\ominus},$$
$$H_2V_{10}O_{28}^{4\ominus},$$

in which anions of this type bind to any desired cations, for example if $H^\oplus$, alkali metal cations, alkaline earth metal cations or noble metal cations, stoichiometrically in such a manner that an electrically neutral-compound is formed.

This behaviour is not limited to vanadium but also applies to the elements niobium and tantalum. Examples which may be mentioned here are the compounds $Nb_2O_5$, $Ta_2O_5$, $NbO_2$, $TaO_2$, $Nb_2O_3$, $NbO$, $Nb(OH)_5$, and $Ta(OH)_5$. Analogously to the vanadium compounds, in the case of niobium and tantalum, polyniobic and polytantalic acids also occur in a wide range of condensation forms.

The capability of forming polycondensation acids, so-called isopoly acids, can be utilised, then, for using a large number of catalytically active oxy compounds of the elements V, Nb and Ta for the purposes of the invention. Depending on which degree of dehydration is produced, oxidic systems having different acid/base character are obtained. These can be mono- or polymetallic systems in which the elements V, Nb and Ta are present in the following atomic ratio:

$V_i + Nb_k + Ta_l$ in which i, k and l are whole or fractional numbers from 0 to 100, with the proviso that the sum of these numbers i, k and l is 100. The value 100 means that the element in question is present in a relative amount of 100 atom percent and the others are consequently present in a relative amount of 0 atom percent. The following list may be mentioned by way of example:

| V | Nb | Ta | Sum (atom percent) |
|---|---|---|---|
| 0 | 60 | 40 | 100 |
| 0 | 100 | 0 | 100 |
| 100 | 0 | 0 | 100 |
| 10 | 30 | 60 | 100 |

Catalysts or catalyst supports can be obtained from the oxidic and hydroxidic systems mentioned by a large number of preparations. Examples are:
1. Preparation of shaped articles from the corresponding oxidic system.
2. Incorporation of additional catalytically active components, for example salts of elements from the group of platinum metals and/or activators in the base material before shaping.
3. Subsequent loading of the previously prepared shaped articles by impregnating, dipping or spraying processes using salts of elements from the group of platinum metals and/or activators.
4. Rolling and/or spraying of mixtures of oxidic or hydroxidic substances onto piece-like materials of any desired composition and origin.
5. Rolling and/or spraying of mixtures of oxidic or hydroxidic substances which already contain the catalytically active salts of elements from the group of platinum metals and/or the activators onto piece-like materials of any desired composition and origin.
6. Subsequent loading of supports prepared according to 4. by impregnating, dipping or spraying processes with the catalytically active salts of elements from the group of platinum metals and/or with the activators.

The amount of addition is 0.1–100 times, preferably 0.2–10 times, the amount of platinum metal, calculated as metal not only for the addition but also for the platinum metal.

The catalyst to be used according to the invention is prepared by methods generally known to one skilled in the art. Thus, the support can be impregnated or sprayed with a solution of one of the platinum metal compounds mentioned. The same procedure is used for the additive or additives mentioned. In the case where it is desired to fix the platinum metal on the support as a metal or in the form of the carbonate, oxide or hydroxide and to activate it only after its introduction into the reactor in the manner described by means of hydrogen halide under the reaction conditions to give the platinum metal halide, the platinum metal compound applied can be reduced to the metal by a suitable reducing agent in a manner known to one skilled in the art or converted into the carbonate, oxide or hydroxide by a suitable precipitant.

Furthermore, it has been observed that in order to obtain uniformly high dialkyl carbonate selectivities, it is advantageous to bring the hydrogen halide into contact with the catalyst over the period during which it is used. However, it was further observed that this amount of hydrogen halide can be substantially less than described in the literature mentioned above. Thus, it is merely necessary to replace the amount of hydrogen halide discharged together with the reaction products and originating from the activated form of the catalyst. This amount can be determined by analysis. It is in general in the range from 1–2000 μg of hydrogen halide per g of dialkyl carbonate formed.

Hydrogen halide for the purposes of the invention is hydrogen fluoride, hydrogen chloride, hydrogen bromide and hydrogen iodide, preferably hydrogen chloride and hydrogen bromide, particularly preferably hydrogen chloride.

The hydrogen halide can be metered into the reaction mixture as such in the form of a gas. However, it can also be metered dissolved in one of the substances present in the reaction mixture, thus, for example, dissolved in the alcohol on which the alkyl nitrite is based.

Catalysts of the type described have a long life (>200 h). In addition to the mechanical stability and abrasion resistance described, they retain their activity and selectivity for an extremely long time.

The catalysts mentioned can be operated under a gas hourly space velocity (GHSV) of 700–5 000 l of the mixture of gaseous reactants per l of catalyst per hour.

The process according to the invention is carried out at a temperature of 50°–150° C., preferably 70°–120° C., particularly preferably 70°–110° C., and a pressure of 0.8–10 bar, preferably 1–7 bar, particularly preferably 1–5 bar.

The alkyl nitrites to be used according to the invention are prepared by known processes, for example from the corresponding alcohol and nitrous acid, which may be formed in situ from an alkali metal nitrite and a mineral acid, such as sulphuric acid. The nitrogen monoxide NO formed in the course of the process according to the invention can be regenerated continuously to alkyl nitrite using oxygen and fresh alcohol (DE-OS (German Published Specification) 3,834,065) and recycled together with unconverted reactants.

EXAMPLES

Catalyst preparation and definitions

Comparative Example 1

100 ml of activated carbon granules were impregnated in a known manner with a solution of PdCl$_2$ and CuCl$_2$ in water, and the product was dried at 80° C. in vacuo (20 mmhg) . The ready-to-use catalyst contained 8 g of Pd/l and 8 g of Cu/l.

The space time yield (STY) in [g/l·h] and for dimethyl carbonate in the examples is calculated by $$\frac{m_{DmC}}{V_{Cat} \cdot t},$$

in which $m_{DmC}$ is the amount of dimethyl carbonate (DMC) formed,
$V_{Cat}$ is the catalyst volume and t is the time.
The selectivity S (%) is calculated by $$S = \frac{n_{DMC}}{n_{DMC} + 2 \times n_{DMO} + n_{MF} + n_{FDA}} \times 100 \, [\%]$$

in which
$n_{DMC}$ = the amount of dimethyl carbonate
$n_{DMO}$ = is the amount of dimethyl oxalate
$n_{MF}$ = is the amount of methyl formate $n_{FDA}$ = is the amount of formaldehyde dimethyl acetal.

Example 1

100 ml of Nb(OH)$_5$, material was impregnated with an aqueous Li$_2$PdCl$_4$ solution, and the product was dried at 80° C. in vacuo (29 mmhg). The catalyst then contained 8 g of Pd/l.

Example 2

100 ml of Ta(OH)$_5$ material was impregnated with an aqueous Li$_2$PdCl$_4$ solution, and the product was dried at 80° C. in vacuo (29 mmHg). The catalyst then contained 8 g of Pd/l.

Example 3

100 ml of V$_2$O$_5$ material was impregnated with an aqueous Li$_2$PdCl$_4$ solution, and the product was dried at 80° C. in vacuo (29 mmhg). The catalyst then contained 8 g of Pd/l.

Description of the experiments

Example 4

In an upright glass tube (length 50 cm, diameter 4 cm), 20 ml of the catalyst from Example 1 was introduced between a packing of Raschig rings.

The glass tube was heated to 90° C., and a gas mixture comprising 45.0% of N$_2$, 22.5% of MeONO, 22.5% of CO and 10.0% of MeOH was passed. The space velocity was 1000 1/l·h. The gas stream leaving the reactor was cooled to 5° C., and the condensed phase obtained was analysed by gas chromatography. The uncondensed products were detected by IR spectroscopy and mass spectroscopy.

Dimethyl carbonate was formed after 2 hours at an STY of 120 g/l·h and a selectivity of 99%. After 10 hours, the STY was 40 g/l·h and the selectivity 99%.

Example 5

The experiment described in Example 4 was repeated, using the product described in Example 2 as the catalyst. Dimethyl carbonate was formed after 2 hours at an STY of 115 g/l·h and a selectivity of 99%. After 10 hours, the STY was 38 g/l·h and the selectivity 98.5%.

Example 6

The experiment described in Example 4 was repeated, using, as the catalyst, the one described in Example 3.

Dimethyl carbonate was formed after 2 hours at an STY of 105 g/l·h and a selectivity of 99%.

After 10 hours, the STY was 35 g/l·h and the selectivity 98.5%.

Example 7

100 ml of Nb(OH)., material was impregnated with a solution comprising 1 part of PdCl$_2$ and 4 parts of AlCl$_3$·6H$_2$O in water, and the product was dried at 80° C. in vacuo (29 mmhg). The catalyst then contained 16 g of Pd/l.

Example 8

In an upright glass tube (length 50 cm, diameter 4 cm), 37.5 ml of the catalyst from Example 7 were arranged between two packings of Raschig rings.

The glass tube was heated to 90° C., and a gas mixture comprising 58.0% of N$_2$, 23.2% of MeONO, 10.5% of CO and 8.3% of MeOH and 0.037% of HCl was passed. The space velocity was 700 1/l·h.

The gas stream leaving the reactor was cooled to 5° C., and the concentrated phase obtained was analysed by gas chromatography. The uncondensed products were detected by IR spectroscopy and mass spectroscopy.

Dimethyl carbonate was formed after 2 hours at an STY of 120 g/l·h and a selectivity of 99%.

After 40 hours, the STY was 110 g/l·h and the selectivity 99%.

What is claimed is:

1. A process for the preparation of a dialkyl carbonate of the formula $$O=C(OR)_2,$$

in which

R represents straight-chain or branched alkyl having up to 4 carbon atoms, by reaction of carbon monoxide (CO) with an alkyl nitrate of the formula

RONO, in which

R has the meaning given, in the presence or absence of an inert gas and in the presence or absence of the parent alcohol ROH and in the presence or absence of NO over a supported metal catalyst at elevated temperature in a continuous gas phase reaction, wherein the supports used are oxidic or hydroxidic compounds of V, Nb, Ta, or combinations thereof, said metal being present in the form of a halide of a metal selected from the group consisting of palladium, platinum, iridium, ruthenium and rhodium, or a complex thereof, in which said metal halide or said halogen-containing metal complex can be generated in situ in the process reactor under the reaction conditions from the metal or a halogen-free metal compound by means of hydrogen halide, the catalyst is furthermore provided with or without an addition of an antimony, bismuth, aluminum, copper, vanadium, niobium, tantalum, tin, iron, cobalt, nickel compound or a mixture of a plurality thereof, and the reaction is carried out at a nitrite:CO volume ratio of 0.1–10:1 and a temperature of 50°–150° C., in which the addition of hydrogen halide is continued in an amount in which the hydrogen halide is discharged from the reactor together with the reaction mixture.

2. The process of claim 1, wherein the reaction is carried out at 70°–120° C.

3. The process of claim 2, wherein the reaction is carried out at 70°–110° C.

4. The process of claim 1, wherein the reaction is carried out at a nitrite:CO volume ratio of 0.2–4:1.

5. The process of claim 4, wherein the reaction is carried out at nitrite:CO volume ratio of 0.3–3:1.

6. The process of claim 1, wherein said metal is selected from the group consisting of palladium, ruthenium and rhodium.

7. The process of claim 6, wherein the metal is palladium.

8. The process of claim 1, wherein said halide is a chloride or bromide.

9. The process of claim 8, wherein said halide is a chloride.

10. The process of claim 1, wherein the catalyst is provided with an addition of an antimony, bismuth, aluminium, vanadium, niobium, tantalum compound or a mixture of a plurality thereof.

11. The process of claim 10, wherein the catalyst is provided with an addition of an aluminum compound.

12. The process of claim 1, wherein the reaction is carried out in the presence of an inert gas, the inert gas being 20–80% by volume of the total gas volume.

13. The process of claim 12, wherein the inert gas is 30–70% volume of the total gas volume.

14. The process of claim 1, wherein the reaction is carried out with a gas hourly space velocity over the catalyst of 700–5000 litres of the mixture of the gaseous reactants per litre of catalyst per hour.

15. The process of claim 1, wherein dimethyl carbonate or diethyl carbonate is prepared by reaction of CO with methyl nitrate or ethyl nitrite.

16. The process of claim 15, wherein dimethyl carbonate is prepared by reaction of CO with methyl nitrite.

17. The process of claim 1, wherein the reaction is carried out at a pressure of 0.8–10 bar.

18. The process of claim 17, wherein the reaction is carried out at a pressure of 1–7 bar.

* * * * *